United States Patent
Shu et al.

(10) Patent No.: US 9,297,050 B1
(45) Date of Patent: Mar. 29, 2016

(54) REMOVING IMPURITIES FROM SUGAR SOLUTIONS

(71) Applicant: Rohm and Haas Company, Philadelphia, PA (US)

(72) Inventors: Yi Shu, Shanghai (CN); Fengshan Luo, Shanghai (CN); Gongwei Pu, Shanghai (CN)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 14/892,781

(22) PCT Filed: May 28, 2013

(86) PCT No.: PCT/CN2013/076300
§ 371 (c)(1),
(2) Date: Nov. 20, 2015

(87) PCT Pub. No.: WO2014/190477
PCT Pub. Date: Dec. 4, 2014

(51) Int. Cl.
| | |
|---|---|
| *C07C 29/32* | (2006.01) |
| *C07C 31/20* | (2006.01) |
| *C13K 13/00* | (2006.01) |
| *C07C 29/00* | (2006.01) |
| *B01D 15/36* | (2006.01) |

(52) U.S. Cl.
CPC ............ *C13K 13/007* (2013.01); *B01D 15/362* (2013.01); *C07C 29/00* (2013.01); *C07C 29/32* (2013.01); *C07C 31/20* (2013.01)

(58) Field of Classification Search
CPC .............................. C07C 31/20; C07C 29/32
USPC ........................................................ 568/852
See application file for complete search history.

(56) References Cited

U.S. PATENT DOCUMENTS

| | | | |
|---|---|---|---|
| 3,214,293 | A | 10/1965 | Mountfort |
| 3,884,714 | A | 5/1975 | Schneider et al. |
| 8,003,353 | B2 | 8/2011 | Quay et al. |

FOREIGN PATENT DOCUMENTS

CN 102286548 A 12/2011

OTHER PUBLICATIONS

Supelco, "Use Ion Exchange Liquid Chromatography for Faster, More Efficient Sugar Refining," Bulletin 911 published by Sigma-Aldrich Co, (1997).

*Primary Examiner* — Elvis O Price
(74) *Attorney, Agent, or Firm* — Carl P. Hemenway

(57) ABSTRACT

Provided is a process for removing impurities from a solution (S1), wherein said solution (S1) comprises one or more sugar dissolved in an aqueous solvent, wherein said solution (S1) has conductivity at 25° C. of 500 µS/cm or higher, and wherein said process comprises (a) contacting said solution (S1) with a cation exchange resin (R1) to produce a solution (S2) in which 80% or more of the cations are all of the same element (E); and (b) then contacting said solution (S2) with a cation exchange resin (R2) in which, prior to said contacting, 90% or more of acid groups are in the salt form with said element (E). Also provided is a process for producing glycols comprising providing an extract solution by the process of claim 1, and then contacting said solution (S3) with hydrogen and a metal catalyst.

6 Claims, No Drawings

REMOVING IMPURITIES FROM SUGAR SOLUTIONS

It is sometimes desirable to purify aqueous sugar solutions that contain undesirably high levels of one or more of the following impurities: one or more salt having monovalent cation, one or more salt having multivalent cation; and one or more colored impurity. One useful source of such solutions is the hydrolysis of cellulose and/or semicellulose. Also, such solutions normally contain high levels of proteins and other impurities. In the past, ion exchange methods were used for the purification of such solutions, but such methods were inefficient. Some previously-known methods involved one or more ion-exchange step that required regeneration of one or more ion exchange resin using mineral acid and caustic, and the use of such acids and alkali is difficult and expensive. It is desired to provide a more-efficient method that effectively removes salts and colored impurities from sugar solutions. For example, it is desired to provide a method in which at least one ion-exchange step is used in which the required regenerant is a salt solution instead of a mineral acid, or use chromatography process to remove salt and color impurities, in which only water is used as eluent. Also, it is desired to provide a process that includes a chromatography step that removes both salt and colored impurities from the sugar solution.

One possible use for purified sugar solutions is the production of glycols using a reaction that involves contacting the sugar solution with hydrogen and a metal catalyst. Such methods of glycol production perform better if the sugar solution is more highly purified. It is also desired to provide improved methods of glycol production that involve the use of sugar solutions that have been purified by more efficient methods.

U.S. Pat. No. 8,003,353 describes a method of obtaining a product sugar stream from a cellulosic biomass. The method described by U.S. Pat. No. 8,003,353 involves the use of exclusion chromatography. It is desired to provide improved methods of purifying sugar solutions.

The following is a statement of the invention.

The first aspect of the present invention is A process for removing impurities from a solution (S1), wherein said solution (S1) comprises one or more sugar dissolved in an aqueous solvent, wherein said solution (S1) has conductivity at 25° C. of 500 µS/cm or higher, and wherein said process comprises (a) contacting said solution (S1) with a cation exchange resin (R1) to produce a solution (S2) in which 80% or more of the cations are all of the same element (E), on a molar basis, based on the total moles of cations in resin (R1); and (b) then contacting said solution (S2) with a cation exchange resin (R2) in which, prior to said contacting, 90% or more of acid groups are in the salt form with said element (E) as the cation, on a molar basis, based on the total moles of acid groups on resin (R2).

The second aspect of the present invention is A process for producing glycols comprising steps (A) providing an extract solution by the process of claim 1, and (B) then contacting said solution (S3) with hydrogen and a metal catalyst.

The following is a detailed description of the invention.

As used herein, the following terms have the designated definitions, unless the context clearly indicates otherwise.

A "solvent" is a composition that is liquid over a temperature range that includes 15° C. to 70° C. A solvent is "aqueous" if it contains 50% or more water by weight based on the weight of the solvent. If the solvent is a mixture of water and another compound, that other compound is miscible with water in the proportions that are used. "Miscible" means that the water and the other compound are distributed throughout each other on a molecular level.

A "solution" is a mixture in which one or more "solute" material is dispersed on a molecular or ionic level throughout a liquid "solvent." The solute is said to be "dissolved" in the solvent.

As used herein, a sugar is a compound, the molecule of which contains exactly one or two saccharose groups. That is, a "sugar" is a monosaccharide or a disaccharide.

"Conductivity" is the electrical conductivity, in units of microSiemens per centimeter (µS/cm). Conductivity is a measure of the total amount of dissolved salts.

The color of a solution of sugar dissolved in an aqueous solvent is assessed by $$\text{Color} = A \times 1{,}000/(B1 * C1)$$

where A is the absorbance of the solution at 420 nm at 25° C., B1 is the optical path length used in the absorbance measurement, and C1 is the concentration of the sugar in the solution in grams per liter. Color is reported in units called "IU."

The concentration of sugar dissolved in an aqueous solvent is described by the quantity "Brix," which is determined as follows. Brix=(((((11758.74*nD−88885.21)*nD+270177.93)*nD−413145.80)*nD+318417.95)*nD−99127.4536) where nD is the refractive index, measured at the wavelength of the sodium D line (589.3 nm) at 20° C.

Ion exchange resins are synthetic organic polymers that exist in the form of individual particles. Volume-median particle size is from 50 µm to 2 mm. Two types of ion exchange resins are cation exchange resins and anion exchange resins.

Cation exchange resins have pendant acidic groups covalently bound to the polymer; cation exchange resins do not have pendant amine groups or ammonium groups covalently bound to the polymer. Strong-acid cation exchange resins have pendant sulfonic acid or sulfonate groups covalently bound to the polymer. An acidic group has a labile hydrogen atom. An acid group may be in the "H form," in which the labile hydrogen atom remains attached to the acid group; alternatively, an acid group may be in the "salt form," in which the labile hydrogen is replaced by a cation.

Anion exchange resins have pendant amine groups or quaternary ammonium groups covalently bound to the polymer; anion exchange resins do not have acidic groups covalently bound to the polymer. Strong-base anion resins have quaternary ammonium groups covalently bound to the polymer.

A collection of particles may be characterized by the "uniformity coefficient," which is defined as the quotient D60/D10. D60 is the opening size of an aperture through which 60% of the particles, on a volume basis, are able to pass, and through which 40% of the particles, on a volume basis, are too large to be able to pass. D10 is the opening size of an aperture through which 10% of the particles, on a volume basis, are able to pass, and through which 90% of the particles, on a volume basis, are too large to be able to pass.

When a ratio is said herein to be X:1 or greater, it is meant that the ratio is Y:1, where Y is greater than or equal to X. For example, if a ratio is said to be 3:1 or greater, that ratio may be 3:1 or 5:1 or 100:1 but may not be 2:1. Similarly, when a ratio is said herein to be W:1 or less, it is meant that the ratio is Z:1, where Z is less than or equal to W. For example, if a ratio is said to be 15:1 or less, that ratio may be 15:1 or 10:1 or 0.1:1 but may not be 20:1.

The practice of the present invention involves the use of a solution, herein labeled "solution (S1)," which contains one or more sugar dissolved in an aqueous solvent. The aqueous solvent contains water in the amount, by weight based on the weight of the solvent, of 50% or more; preferably 75% or more; more preferably 90% or more. Preferably, the amount of the sugar in solution (S1) that is in the form of monosaccharides is, by weight based on the weight of all sugars, 50% or more; more preferably 75% or more; more preferably 95% or more.

The conductivity of solution (S1) is 5000/cm or higher; preferably 750 µS/cm or higher; more preferably 1000 µS/cm or higher. The Brix of solution (S1) is preferably 15 or higher; more preferably 30 or higher. The color of solution (S1) is preferably 500 IU or higher; more preferably 600 IU or higher; more preferably 800 IU or higher; more preferably 1,000 IU or higher.

Solution (S1) may be made by any method. One preferred method is hydrolysis of cellulose and/or semicellulose.

The process of the present invention involves step (a), which is contacting solution (S1) with a cation exchange resin, herein labeled "cationic exchange resin (R1)" or synonymously "resin (R1)." The composition of resin (R1) is preferably selected from styrenic polymers, acrylic polymers, phenolic polymers, and polyalkylamine polymers. Preferred are styrenic polymers. Preferred polymers are crosslinked; more preferably, the polymer has sufficient crosslink density that the polymer is not soluble in any solvent.

Styrenic polymers are polymers that contain 50% or more by weight based on the weight of the polymer, polymerized units of styrenic monomers. Styrenic monomers are compounds that contain one or more aromatic ring and one or more vinyl group bonded directly to an aromatic ring. Preferred styrenic monomers are styrene, divinylbenzene, and mixtures thereof. Among styrenic polymers, preferred are those in which the amount of polymerized units of styrenic monomers is 75% or more; more preferred is 90% or more; more preferred is 99% or more.

Acrylic polymers are polymers that contain 30% or more by weight based on the weight of the polymer, polymerized units of acrylic monomers. Acrylic monomers are acrylic acid, methacrylic acid, esters thereof, amides thereof, and mixtures thereof. Phenolic polymers contain the reaction products of a phenol-type compound with an aldehyde. Phenol-type compounds include phenol, isomers of cresol, isomers of xylenol, resorcinol, and phenols substituted with one or more alkyl or aromatic group. Aldehydes include formaldehyde and furfural. Polyalkylamine polymers contain the reaction products of polyamines with epichlorohydrin. Polyamines are alkyl compounds substituted with two or more amine groups.

Among styrenic and acrylic polymers, it is useful to characterize the amount of polymerized units of multifunctional monomer. A multifunctional monomer has two or more vinyl groups that are capable of free radical polymerization. Preferred multifunctional monomer is divinylbenzene. Preferably the amount of polymerized units of multifunctional monomer is, by weight based on the weight of polymer, 15% or less; more preferably 12% or less; more preferably 10% or less. Preferably the amount of polymerized units of multifunctional monomer is, by weight based on the weight of polymer, 1% or more.

Preferably, resin (R1) is a macroporous resin. Preferably, resin (R1) is made with the use of a porogen. Preferably, the average pore size in resin (R1) on a number basis is 5 nm or more.

Preferably, resin (R1) is a strong acid cation exchange resin. Preferably, resin (R1) has sulfonic acid groups covalently bonded to the polymer.

Preferably, prior to contact with solution (S1), the proportion of the acid groups that are bonded to resin (R1) that are in salt form is, on a molar basis based on the total moles of acid groups bonded to resin (R1), 50% or more; more preferably 75% or more; more preferably 90% or more.

Preferably, prior to contact with solution (S1), the acid groups bonded to resin (R1) that are in the salt form mostly have the same associated cation. Preferably, there exists a single element (E) such that, among the cations associated with acid groups bonded to resin (R1) that are in salt form, on a molar basis based on the total moles of cations associated with such acid groups, 80% or more are all cations of the same element (E); more preferably 90% or more; more preferably 95% or more. Element (E) is preferably calcium, potassium, or sodium; more preferably potassium or sodium; more preferably sodium. That is, the cation is preferably $Ca^{+2}$, $K^+$, or $Na^+$; more preferably $K^+$ or $Na^+$; more preferably $Na^+$.

Preferably, step (a) is performed as an ion exchange process. Preferably, a portion of solution (S1) is added to the top of a chromatography column that contains resin (R1) and is allowed to pass through that column. In the performance of step (a), service flow rate is preferably 1 bed volume per hour (BV/hr) or more; more preferably 2 BV/hr or more; more preferably 5 BV/hr or more. In the performance of step (a), service flow rate is preferably 50 BV/hr or less; more preferably 20 BV/hr or less. Preferably, step (a) is performed at a temperature of from 20° C. to 80° C.

In preferred embodiments, resin (R1) can be regenerated with a salt solution. For example, if element (E) is sodium, resin (R1) can be regenerated with NaOH or NaCl.

After step (a) is performed, the remaining solution is now "solution (S2)." Resin (R1) is preferably separated from the solution (S2). Most of the cations in solution (S2) will be of element E, the same element that was present on most of the acid groups that were present on resin (R1) prior to the contact of resin (R1) with solution (S1). Preferably, the proportion of cations in solution (S2), on a molar basis based on all the cations in solution (S2), that are of element (E) is 80% or more; more preferably 90% or more; more preferably 95% or more.

Preferably, the concentration of acetate anion in solution (S2) is either zero or is less than 5% by weight, based on the weight of solution (S2).

Solution (S2) is brought into contact with a cation exchange resin herein called "cation exchange resin (R2)" or synonymously "resin (R2)." Resin (R2) may be different from resin (R1) or may be identical to resin (R1). The preferred compositions and characteristics described herein above regarding resin (R1) also apply, independently, to resin (R2).

Preferably, the uniformity coefficient of resin (R2) is 1.5 or lower; more preferably 1.2 or lower. Preferably, the median particle diameter, on a volume basis, of resin (R2) is 600 µm or lower; more preferably 400 µm or lower. Preferably, the median particle diameter, on a volume basis, of resin (R2) is 100 µm or higher; more preferably 200 µm or higher.

The preferred compositions and characteristics described herein above regarding solution (S1) also apply, independently, to solution (S2), as solution (S2) exists prior to contact with resin (R2). When solution (S1) contains a relatively high concentration of multivalent cations, it is contemplated that solution (S2) may have a higher conductivity than solution (S1), because the change from solution (S1) to solution (S2) involves replacing each multivalent cations with monovalent cations. Independently, in some embodiments step (a) will remove some of the color from solution (S1); in such embodiments, the ratio of the color of solution (S2) to the color of solution (S1) is 0.95:1 or less; or 0.9:1 or less.

The practice of the present invention involves step (b), bringing solution (S2) into contact with resin (R2). After solution (S2) has been in contact with resin (R2), preferably resin (R2) is separated from the remaining solution, and the remaining solution herein is referred to as the "extract" solution.

The extract solution is a purified sugar solution. Preferably, the conductivity of the extract solution is 100 µS/cm or lower; more preferably 50 µS/cm or lower. Preferably the color or the extract solution is 200 IU or lower; more preferably 100 IU or lower; more preferably 50 IU or lower. Preferably, the extract solution has Brix of 4 or higher; more preferably 6 or higher; more preferably 10 or higher; more preferably 20 or higher.

Preferably, step (b) is performed as an ion exclusion chromatography step. That is, it is contemplated that because the cations on resin (R2) are the same as the cations in solution (S2), the cations in solution (S2) will be repelled by the resin (R2) and therefore the salts in solution (S2) will move through resin (R2) quickly relative to the sugar dissolved in solution (S2). Ion exclusion chromatography may be performed in any mode, including pulse mode, simulated moving bed mode, improved simulated moving bed, or sequential simulated moving bed mode. It is contemplated that the retention times of the salts in solution (S2) and the sugars in solution (S2) may be assessed and that the retention time of the salts will be lower.

When step (b) is performed as an ion exclusion chromatography step, it is contemplated that the following separate solutions may be collected from the process of step (b): the "extract" solution described herein above, which has relatively high concentration of sugar and relatively low concentration of salts, and a "raffinate" solution that has a relatively high concentration of salts and a relatively low concentration of sugar.

The extract solution may be used for any purpose, for example the extract solution may be used as raw material for a subsequent chemical or biochemical process, such as the formation of ethanol or the formation of glycols. For some intended uses, it will be desirable to further purify the extract solution. A preferred use for the extract solution is as raw material for the production of glycols, preferably ethylene glycol or propylene glycol or a mixture thereof. A preferred method of producing glycols is to contact a sugar solution with hydrogen and with an appropriate metal catalyst. For such a method of producing glycols, it is desirable that the sugar solution have conductivity of 10 µS/cm or lower.

Preferably, the process of the present invention comprises an additional step, herein labeled step "(c)," performed after step (b). In step (c), the extract solution is brought into contact with a cation exchange resin (herein called "resin (CR3)") and with an anion exchange resin (herein called "resin (AR3)"). The extract solution may be brought into contact with resin (CR3) and resin (AR3) sequentially in either order or simultaneously. Preferably, a mixture (herein called "resin (MB3)") of resin (CR3) and resin (AR3) is prepared and brought into contact with the extract solution.

Preferably, resin (CR3) is a strong-acid type resin. Preferably, resin (CR3) is a crosslinked styrenic polymer. Preferably, resin (CR3) is a macroporous (synonymously called macroreticular) resin. Preferably, the average pore size on a number basis of resin (CR3) is 50 nm or more; more preferably 100 nm or more. Preferably, resin (AR3) resin is a strong-base type resin. Preferably, resin (AR3) is a crosslinked styrenic polymer. Preferably, resin (AR3) is a macroporous (synonymously called macroreticular) resin. Preferably, the average pore size on a number basis of resin (AR3) is 50 nm or more; more preferably 100 nm or more.

Preferably, resin (MB3) is used. Preferably, the weight ratio of resin (CR3) to resin (AR3) is 0.5:1 or higher; more preferably 0.75:1 or higher; more preferably 0.9:1 or higher. Preferably, the weight ratio of resin (CR3) to resin (AR3) is 2:1 or less; more preferably 1.33:1 or less; more preferably 1.1:1 or less.

Preferably, if step (c) is performed, step (c) is performed as an ion exchange process. Preferably, a portion of extract solution is added to the top of a chromatography column that contains resin (MB3), and additional aqueous solvent is then added to the column. Preferably, the amount of water in the additional aqueous solvent, by weight based on the weight of the additional aqueous solvent, is 95% or more; more preferably 99% or more. Preferably, the conductivity of the additional aqueous solvent is 10 µS/cm or lower. In the performance of step (c), service flow rate is preferably 1 bed volume per hour (BV/hr) or more; more preferably 2 BV/hr or more; more preferably 5 BV/hr or more. In the performance of step (a), service flow rate is preferably 50 BV/hr or less; more preferably 20 BV/hr or less. Preferably, step (a) is performed at a temperature of from 20° C. to 45° C.

The following are examples of the present invention.

EXAMPLE 1

Step (a) was performed as follows. Initial sugar solution had conductivity of 2280 S/cm, Brix of 31, and pH=4.78. Sugar solution was passed through a chromatography column packed with AMBERLITE™ 200CNa resin (Dow Chemical Co.). Service flow rate was 9 BV/hr. A sample of 70 ml was collected from the end of the column and discarded. A sample of 210 ml was then collected (sample "A"). Sample A had conductivity of 3320 µS/cm, Brix of 32, and pH=4.88. It is considered that cations in the initial sugar solution were replaced with $Na^+$ ions in sample A.

Step (b) was performed as follows. The pulse method was used. A chromatography column was prepared and packed with AMBERLITE CR1310Na resin (Dow Chemical Co.). Sample A was placed on the top of the column, and chromatography was performed as follows: flow rate=2BV/hr; resin bed volume=120 ml; resin bed height=76 cm; sampling from 0.2BV to 1.5BV, 0.05BV per collection; eluent=water; injected feed volume=4.8 ml. Each sample was evaluated for Brix with a QuickBrix90™ meter (Mettlo), and the absorbance was measured at 420 nm.

Results were as follows:

| Bed Volume | Conductivity (µS/cm) | Brix | Absorbance at 420 nm |
|---|---|---|---|
| 0.2 | 31 | 0 | 0.013228 |
| 0.25 | 39 | 0 | 0.013228 |
| 0.3 | 43 | 0 | 0.017729 |
| 0.35 | 45 | 0 | 0.017729 |
| 0.4 | 46 | 0 | 0.017729 |
| 0.45 | 391 | 0 | 0.036212 |
| 0.5 | 2434 | 0.8 | 0.154902 |
| 0.55 | 2884 | 1 | 0.148742 |
| 0.6 | 383 | 1.4 | 0.075721 |
| 0.65 | 411 | 2.2 | 0.045757 |
| 0.7 | 198 | 4.4 | 0.036212 |
| 0.75 | 112 | 6.5 | 0.036212 |
| 0.8 | 74 | 5.4 | 0.031517 |
| 0.85 | 62 | 2.8 | 0.026872 |

-continued

| Bed Volume | Conductivity (µS/cm) | Brix | Absorbance at 420 nm |
|---|---|---|---|
| 0.9 | 57 | 1 | 0.022276 |
| 0.95 | 53 | 0.4 | 0.017729 |
| 1 | 53 | 0 | 0.017729 |
| 1.05 | 51 | 0 | 0.017729 |
| 1.1 | 53 | 0 | 0.017729 |
| 1.15 | 56 | 0 | 0.017729 |
| 1.2 | 54 | 0 | 0.017729 |
| 1.25 | 53 | 0 | 0.017729 |
| 1.3 | 57 | 0 | 0.017729 |
| 1.35 | 51 | 0 | 0.017729 |
| 1.4 | 48 | 0 | 0.017729 |

Color and conductivity were eluted almost together and faster than sugar (Brix) in the column. The separation resolution was assessed by band width and peak position. The Brix of the eluent was recorded as a function of elution time. Elution time is measured in bed volumes (BV). The elution time of the peak value of Brix is VBr; the elution time of the peak value of Color is VIU, and the elution time of the peak value of conductivity is VCond. The Brix was plotted as a function of elution time, and a Brix peak was formed. The width of the Brix peak (WBr) was the width of the segment of the peak base intercepted by the tangents drawn to the inflection points on either side of the peak (following the method of the International Union of Pure and Applied Chemistry *IUPAC. Compendium of Chemical Terminology*, 2nd ed. (the "Gold Book"), Compiled by A. D. McNaught and A. Wilkinson. Blackwell Scientific Publications, Oxford (1997)). Similarly, the width of the Color peak (WIU) and the width of the conductivity peak (WCond) were determined.

Separation resolution between Brix and color (RBC) was determined as

RBC=2*(VBr−VIU)/(WBR+WIU).

Similarly, resolution between Brix and conductivity (RCond) was determined as

RCond=2*(VBr−VCond)/(WBR+WCond).

Both RBC and RCond were greater than 0.3. From this result it is concluded that the pulse method was successful in purifying the sugar solution and that a sequential simulated moving bed method would also be successful. It is noted that step (b) produced a sugar solution from which substantial amounts of both salts and colored impurities had been removed.

The invention claimed is:

1. A process for removing impurities from a solution (S1), wherein said solution (S1) comprises one or more sugar dissolved in an aqueous solvent, wherein said solution (S1) has conductivity at 25° C. of 500 µS/cm or higher, and wherein said process comprises
    (a) contacting said solution (S1) with a cation exchange resin (R1) to produce a solution (S2) in which 80% or more of the cations are all of the same element (E), on a molar basis, based on the total moles of cations in resin (R1); and
    (b) then contacting said solution (S2) with a cation exchange resin (R2) in which, prior to said contacting, 90% or more of acid groups are in the salt form with said element (E) as the cation, on a molar basis, based on the total moles of acid groups on resin (R2).

2. The process of claim 1 wherein said sugar comprises one or more monosaccharide.

3. The process of claim 1 wherein said solution (S1) has conductivity of 750 µS/cm.

4. The process of claim 1 wherein said solution (S1) has color of 500 IU.

5. The process of claim 1 wherein said process additionally comprises the steps:
    after said step (b), separating said resin (R2) from the extract solution resulting from said step (b), and
    bringing said extract solution into contact with a cation exchange resin (CR3) and with an anion exchange resin (AR3).

6. A process for producing glycols comprising steps
    (A) providing an extract solution by the process of claim 1, and
    (B) then contacting said solution (S3) with hydrogen and a metal catalyst.

* * * * *